US011536731B2

(12) United States Patent
Makhatadze et al.

(10) Patent No.: US 11,536,731 B2
(45) Date of Patent: Dec. 27, 2022

(54) SYSTEMS AND METHODS FOR BINDING AMYLOID FIBRILS USING FLUORESCENT PROTEIN

(71) Applicant: RENSSELAER POLYTECHNIC INSTITUTE, Troy, NY (US)

(72) Inventors: George I. Makhatadze, Clifton Park, NY (US); Changmingzi Xu-Fuery, Stephentown, NY (US); Josephine Grace LoRicco, Coventry, CT (US); Nathan James, Clay, NY (US); Anthony Charles Bishop, Glastonbury, CT (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/480,216

(22) PCT Filed: Jan. 23, 2018

(86) PCT No.: PCT/US2018/014770
§ 371 (c)(1),
(2) Date: Jul. 23, 2019

(87) PCT Pub. No.: WO2018/136910
PCT Pub. Date: Jul. 26, 2018

(65) Prior Publication Data

US 2019/0383835 A1 Dec. 19, 2019

Related U.S. Application Data

(60) Provisional application No. 62/449,238, filed on Jan. 23, 2017, provisional application No. 62/619,948, filed on Jan. 22, 2018.

(51) Int. Cl.
*G01N 33/68* (2006.01)
*G01N 21/64* (2006.01)

(52) U.S. Cl.
CPC ..... *G01N 33/6896* (2013.01); *G01N 21/6428* (2013.01); *G01N 2021/6439* (2013.01); *G01N 2560/00* (2013.01); *G01N 2800/2814* (2013.01); *G01N 2800/52* (2013.01)

(58) Field of Classification Search
CPC ........... G01N 33/6896; G01N 21/6428; G01N 2021/6439; G01N 2560/00; G01N 2800/2814; G01N 2800/52; G01N 2800/7047
See application file for complete search history.

(56) References Cited

U.S. PATENT DOCUMENTS

| | | | | |
|---|---|---|---|---|
| 6,399,314 | B1 | 6/2002 | Krishnamurthy | |
| 8,679,768 | B2 | 3/2014 | Kim et al. | |
| 2004/0224365 | A1 | 11/2004 | Glabe et al. | |
| 2007/0093415 | A1 | 4/2007 | Martin | |
| 2010/0129847 | A1 | 5/2010 | Navarrete Santos et al. | |
| 2013/0135580 | A1 | 5/2013 | Hartung et al. | |
| 2015/0125396 | A1 | 5/2015 | Feuerstein et al. | |
| 2016/0077110 | A1 * | 3/2016 | Jara .................... | G01N 33/6896 435/7.92 |

OTHER PUBLICATIONS

Xu et al. Sequence-independent recognition of the amyloid structural motif by GFP protein family. Proceedings of the National Academy of Sciences Sep. 2020, 117 (36) 22122-22127; DOI: 10.1073/pnas.2001457117.*

International Search Report and The Written Opinion, International Application No. PCT/US2018/014770 dated Jan. 23, 2018, mailed May 15, 2018.

Takahashi, T. , Ohta, K. and Mihara, H. (2010), Rational design of amyloid β peptide-binding proteins: Pseudo-Aβ β-sheet surface presented in green fluorescent protein binds tightly and preferentially to structured Aβ. Proteins, 78: 336-347.

* cited by examiner

*Primary Examiner* — Gregory S Emch
(74) *Attorney, Agent, or Firm* — Murtha Cullina LLP; Anthony P. Gangemi

(57) ABSTRACT

Methods and systems directed to monitoring for the presence or progression of amyloid diseases via detection of amyloid fibrils in a sample from an individual are disclosed. An individual, or sample from an individual, is treated with a reagent including a fluorescent protein. The fluorescent protein in the reagent binds to amyloid fibrils present in the sample. Detecting a signal from fluorescent protein bound to the treated sample indicates the presence of amyloid fibrils in the sample and possible diagnosis of an amyloid disease. The presence and progression of an amyloid disease is monitored by quantifying signal intensity from samples taken over time. Treatment with a reagent including a fluorescent protein inhibits amyloid fibril formation by providing the reagent to an environment including amyloid monomers. The fluorescent protein binds to amyloid oligomers during the lag phase and/or elongation phase of amyloid fibril formation, preventing formation of mature amyloid fibrils.

20 Claims, 6 Drawing Sheets

Specification includes a Sequence Listing.

```
SEQUENCE LISTING

<160> NUMBER OF SEQ ID NOS: 101

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1

ctcagctgtc ggcaacagtc gccgatcagg gcgactcacg accagactgt gc            52


<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2

gagtcctgtc ggtctcagtc gccgatcagg gcgactcgtc tgtcatgccg tc            52


<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3

cctacgatct cacgccagtc gccgatcagg gcgactccac acgatgcatg cc            52


<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4

ctgcacgact gaggtcagtc gccgatcagg gcgactggcg ttcgcatttg gc            52


<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5

gcatcaggta gccaggagtc gccgatcagg gcgactgctt cagctgagag gc            52
```

-continued

```
<210> SEQ ID NO 6
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6

ctggctcgaa aatgccagtc gccgatcagg gcgactccaa cctaagccgg ag             52


<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7

cgctatgttc aaggtcagtc gccgatcagg gcgactcatc tgacgttacc tg             52


<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8

cagctgagga aatcttatac gcctccggcc attggctggc gcagcgctct                50


<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9

aagctgtaca tcgtttgaga tgaagcctac gatacatgcc cggcacagtc                50


<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10

caggactcca gcagggcatg agttagatcc attggctggc gcagcgctct                50


<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11

aagctgtaca tcgtttgaga ttcctaacgt accaacgcac gggacggcat                50
```

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 12
atcgtaggtc tgccctgact tctatgcccc attggctggc gcagcgctct 50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 13
aagctgtaca tcgtttgaga tcagaggaca acttcctacg taggcatgca 50

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 14
tcgtgcagtg gtcggattct caactcgtcc attggctggc gcagcgctct 50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 15
aagctgtaca tcgtttgaga ttaagatgaa gataggccac ccgccaaatg 50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 16
cctgatgcct ctttcaacgg cgtattaagc attggctggc gcagcgctct 50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 17
aagctgtaca tcgtttgaga tttcgtctgc atgagtgatg tcgcctctca 50

<210> SEQ ID NO 18

-continued

```
<211> LENGTH: 57
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 18

cagctgagtt tttttgaaat cttatacgcc tccggccatt ggctggcgca gcgctct       57


<210> SEQ ID NO 19
<211> LENGTH: 57
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19

aagctgtaca tcgtttgaga tgaagcctac gatacatgcc cgtttttttg cacagtc       57


<210> SEQ ID NO 20
<211> LENGTH: 57
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20

caggactctt tttttcagca gggcatgagt tagatccaag tcaactcatg cagagac       57


<210> SEQ ID NO 21
<211> LENGTH: 57
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21

ttgctcacca gaacgagtag ttcctaacgt accaacgcac ggtttttttg acggcat       57


<210> SEQ ID NO 22
<211> LENGTH: 57
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22

atcgtaggtt ttttttctgc cctgacttct atgcccgcat gaactataga ctgcgtc       57


<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23

gagcacacta gcacactcat ccagaggaca acttcctacg tatttttttg gcatgca       57


<210> SEQ ID NO 24
<211> LENGTH: 57
```

-continued

<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 24
tcgtgcagtt tttttggtc ggattctcaa ctcgtcgatg aataaggctt gcccggt 57

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 25
gatgaataag gcttgccctg ttaagatgaa gataggccac cctttttttg ccaaatg 57

<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 26
cctgatgctt tttttctctt tcaacggcgt attaagacgg ctacagaggc tttgagg 57

<210> SEQ ID NO 27
<211> LENGTH: 57
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 27
ctatttttgc ggatggctta gttcgtctgc atgagtgatg tctttttttg cctctca 57

<210> SEQ ID NO 28
<211> LENGTH: 57
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 28
cgagccagtt tttttcggat cgtactatgg ttgccttagc atcggaacga gggtaag 57

<210> SEQ ID NO 29
<211> LENGTH: 57
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 29
tcgactgtac caagagccat ccttgaacca ccacagctta cgtttttttc tccggct 57

<210> SEQ ID NO 30
<211> LENGTH: 57
<212> TYPE: DNA

-continued

<213> ORGANISM: Artificial Sequence
<220> FEATURE:
<223> OTHER INFORMATION: Description of Artificial Sequence: Synthetic
      Oligonucleotide

<400> SEQUENCE: 30
acatagcgtt tttttctgga ggtggcatcc tactgttgcg ccgacaatga caactac        57

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 31
cgattgtagc tgaggcttgc tagtacggtg tctggaagtt tcttttttc aggtaac        57

<210> SEQ ID NO 32
<211> LENGTH: 8
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 32 gttgccga        8

<210> SEQ ID NO 33
<211> LENGTH: 8
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 33 tggtcgtg        8

<210> SEQ ID NO 34
<211> LENGTH: 8
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 34 gagaccga        8

<210> SEQ ID NO 35
<211> LENGTH: 8
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 35 gacagacg        8

<210> SEQ ID NO 36
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 36 ggcgtgag 8

<210> SEQ ID NO 37
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 37 tcgtgtgg 8

<210> SEQ ID NO 38
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 38 gacctcag 8

<210> SEQ ID NO 39
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 39 cgaacgcc 8

<210> SEQ ID NO 40
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 40 cctggcta 8

<210> SEQ ID NO 41
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 41 gctgaagc 8

<210> SEQ ID NO 42
<211> LENGTH: 8
<212> TYPE: DNA
<213> ORGANISM: Artificial Sequence
<220> FEATURE:

<223> OTHER INFORMATION: Description of Artificial Sequence: Synthetic
Oligonucleotide

<400> SEQUENCE: 42 ggcatttt 8

<210> SEQ ID NO 43
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 43 taggttgg 8

<210> SEQ ID NO 44
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 44 gaccttga 8

<210> SEQ ID NO 45
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 45 gtcagatg 8

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 46
gcaccgggag ggagggaggg ctttt 25

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 47
ttcctctacc accta 15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 48
taggtggtag aggaa 15

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 49
gatctaactc atgccctgct gtttcgggca tgtatcgtag gcttc 45

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 50
gggcatagaa gtcagggcag atttccgtgc gttggtacgt tagga 45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 51
gacgagttga gaatccgacc attttacgta ggaagttgtc ctctg 45

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 52
cttaatacgc cgttgaaaga gtttgggtgg cctatcttca tctta 45

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 53
gccggaggcg tataagattt ctttgacatc actcatgcag acgaa 45

<210> SEQ ID NO 54
<211> LENGTH: 45
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 54
gccggaggcg tataagattt ctttcgtaag ctgtggtggt tcaag        45

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 55
gccggaggcg tataagattt ctttgaaact tccagacacc gtact        45

<210> SEQ ID NO 56
<211> LENGTH: 49
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 56
atctcaaacg atgtacagct ttttttttag agcgctgcgc cagccaatg    49

<210> SEQ ID NO 57
<211> LENGTH: 49
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 57
actactcgtt ctggtgagca attttttgt ctctgcatga gttgacttg     49

<210> SEQ ID NO 58
<211> LENGTH: 49
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 58
gatgagtgtg ctagtgtgct ctttttttga cgcagtctat agttcatgc    49

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 59
acagggcaag ccttattcat cttttttac cgggcaagcc ttattcatc     49

<210> SEQ ID NO 60
<211> LENGTH: 49
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 60
ctaagccatc cgcaaaaata gtttttttcc tcaaagcctc tgtagccgt 49

<210> SEQ ID NO 61
<211> LENGTH: 49
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 61
gatggctctt ggtacagtcg atttttttct taccctcgtt ccgatgcta 49

<210> SEQ ID NO 62
<211> LENGTH: 49
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 62
agcaagcctc agctacaatc gttttttttgt agttgtcatt gtcggcgca 49

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 63
cagctgagtt t 11

<210> SEQ ID NO 64
<211> LENGTH: 8
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 64 gcacagtc 8

<210> SEQ ID NO 65
<211> LENGTH: 16
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 65
atcgtaggga cggcat 16

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 66
tcgtgcaggg catgca 16

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 67
cctgatgcgc caaat 15

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 68
caggactcgc acagtc 16

<210> SEQ ID NO 69
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 69
gttgccgaca gctgaggaaa tcttatacgc ctccggccat tggctggcgc agcgctct 58

<210> SEQ ID NO 70
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 70
aagctgtaca tcgtttgaga tgaagcctac gatacatgcc cggcacagtc tggtcgtg 58

<210> SEQ ID NO 71
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 71
gagaccgaca ggactccagc agggcatgag ttagatccat tggctggcgc agcgctct 58

<210> SEQ ID NO 72
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 72
aagctgtaca tcgtttgaga ttcctaacgt accaacgcac gggacggcat gacagacg 58

<210> SEQ ID NO 73
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 73
ggcgtgagat cgtaggtctg ccctgacttc tatgccccat tggctggcgc agcgctct 58

<210> SEQ ID NO 74
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 74
aagctgtaca tcgtttgaga tcagaggaca acttcctacg taggcatgca tcgtgtgg 58

<210> SEQ ID NO 75
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 75
gacctcagtc gtgcagtggt cggattctca actcgtccat tggctggcgc agcgctct 58

<210> SEQ ID NO 76
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 76
aagctgtaca tcgtttgaga ttaagatgaa gataggccac ccgccaaatg cgaacgcc 58

<210> SEQ ID NO 77
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 77
cctggctacc tgatgcctct ttcaacggcg tattaagcat tggctggcgc agcgctct 58

<210> SEQ ID NO 78
<211> LENGTH: 58
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 78
aagctgtaca tcgtttgaga tttcgtctgc atgagtgatg tcgcctctca gctgaagc 58

```
<210> SEQ ID NO 79
<211> LENGTH: 65
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 79

gttgccgaca gctgagtttt tttgaaatct tatacgcctc cggccattgg ctggcgcagc     60

gctct                                                                 65


<210> SEQ ID NO 80
<211> LENGTH: 65
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 80

aagctgtaca tcgtttgaga tgaagcctac gatacatgcc cgtttttttg cacagtctgg     60

tcgtg                                                                 65


<210> SEQ ID NO 81
<211> LENGTH: 65
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 81

gagaccgaca ggactctttt tttcagcagg gcatgagtta gatccaagtc aactcatgca     60

gagac                                                                 65


<210> SEQ ID NO 82
<211> LENGTH: 65
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 82

ttgctcacca gaacgagtag ttcctaacgt accaacgcac ggtttttttg acggcatgac     60

agacg                                                                 65


<210> SEQ ID NO 83
<211> LENGTH: 65
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 83

ggcgtgagat cgtaggtttt ttttctgccc tgacttctat gcccgcatga actatagact     60

gcgtc                                                                 65


<210> SEQ ID NO 84
<211> LENGTH: 65
```

<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 84
gagcacacta gcacactcat ccagaggaca acttcctacg tatttttttg gcatgcatcg 60
tgtgg 65

<210> SEQ ID NO 85
<211> LENGTH: 65
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 85
gacctcagtc gtgcagtttt ttttggtcgg attctcaact cgtcgatgaa taaggcttgc 60
ccggt 65

<210> SEQ ID NO 86
<211> LENGTH: 65
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 86
gatgaataag gcttgccctg ttaagatgaa gataggccac cctttttttg ccaaatgcga 60
acgcc 65

<210> SEQ ID NO 87
<211> LENGTH: 65
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 87
cctggctacc tgatgctttt tttctctttc aacggcgtat taagacggct acagaggctt 60
tgagg 65

<210> SEQ ID NO 88
<211> LENGTH: 65
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 88
ctatttttgc ggatggctta gttcgtctgc atgagtgatg tctttttttg cctctcagct 60
gaagc 65

<210> SEQ ID NO 89
<211> LENGTH: 65
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 89
ggcattttcg agccagtttt tttcggatcg tactatggtt gccttagcat cggaacgagg 60
gtaag 65

<210> SEQ ID NO 90
<211> LENGTH: 65
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 90
tcgactgtac caagagccat ccttgaacca ccacagctta cgtttttttc tccggcttag 60
gttgg 65

<210> SEQ ID NO 91
<211> LENGTH: 65
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 91
gaccttgaac atagcgtttt tttctggagg tggcatccta ctgttgcgcc gacaatgaca 60
actac 65

<210> SEQ ID NO 92
<211> LENGTH: 65
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 92
cgattgtagc tgaggcttgc tagtacggtg tctggaagtt tctttttttc aggtaacgtc 60
agatg 65

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 93
gttgccgaca gctgagttt 19

<210> SEQ ID NO 94
<211> LENGTH: 16
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 94
gcacagtcgc tgaagc 16

<210> SEQ ID NO 95
<211> LENGTH: 32
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 95
ggcgtgagat cgtagggacg gcatgacaga cg 32

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 96
gacctcagtc gtgcagggca tgcatcgtgt gg 32

<210> SEQ ID NO 97
<211> LENGTH: 31
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 97
cctggctacc tgatgcgcca aatcgaacgc c 31

<210> SEQ ID NO 98
<211> LENGTH: 32
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 98
gagaccgaca ggactcgcac agtctggtcg tg 32

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 99
caggttatgg cactgtcacg at 22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 100
ccatctgcag caacaccatc tc 22

-continued

```
<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 101

ctctccgaga acaggcctcg act                                          23
```

SYSTEMS AND METHODS FOR BINDING AMYLOID FIBRILS USING FLUORESCENT PROTEIN

CROSS REFERENCE TO RELATED APPLICATION(S)

This application is a national stage patent application filing of International Patent Application No. PCT/US2018/014770, filed Jan. 23, 2018, which claims the benefit of U.S. Provisional Application Nos. 62/449,238, filed Jan. 23, 2017, and 62/619,948, filed Jan. 22, 2018, which are incorporated by reference as if disclosed herein in their entirety.

BACKGROUND

Amyloid fibrils are insoluble aggregates of enzymes, proteins, polypeptides, peptides, and hormones that form long, ordered fibers including β-sheet structures. In the human body, formation of amyloid fibril related species, including protofibrils, mature fibrils and oligomers has been associated with more than 20 human diseases, including neurodegenerative diseases, e.g., Huntington's disease, Alzheimer's disease, Parkinson's disease, fatal familial insomnia, familial amyloid polyneuropathy, atherosclerosis, cerebral amyloid angiopathy, transmissible spongiform encephalopathy; and diseases affecting other organs, e.g., the liver, pancreas, heart, thyroid, such as diabetes mellitus type 2, medullary carcinoma of the thyroid, cardiac arrhythmias, isolated atrial amyloidosis, rheumatoid arthritis, aortic medial amyloid, prolactinomas, heredity non-neuropathic systemic amyloidosis, dialysis related amyloidosis, Finnish amyloidosis, lattice corneal dystrophy, systemic AL amyloidosis, sporadic inclusion body myositis, etc. In addition, amyloid fibrils present in the seminal fluid have been shown to enhance HIV infectivity. Currently there is no cure for these diseases and in many cases even diagnostics, i.e., identification of the presence of amyloid fibril related species, can be performed only on postmortem tissues.

SUMMARY

Some embodiments of the disclosed subject matter are directed to a method of detecting amyloid fibril related species. Some embodiments of the disclosed subject matter are directed to a method of monitoring for the presence or progression of amyloid diseases. In some embodiments, the method includes providing a sample from an individual to be monitored. In some embodiments, the method includes providing a sample including amyloid fibril related species. In some embodiments, the method includes treating the sample with a reagent including a fluorescent protein. In some embodiments, the method includes binding the fluorescent protein to amyloid fibril related species. In some embodiments, the method includes detecting a signal from fluorescent protein bound to the treated sample utilizing, e.g, confocal microscopy, fluorescent microscopy, fluorescent spectroscopy, absorption spectroscopy, ELISA, mass spectroscopy, radioactive detection, etc., or combinations thereof. In some embodiments, the method includes quantifying amyloid fibril related species in said treated sample via quantification of fluorescent protein.

In some embodiments, the fluorescent protein is a cnidarian fluorescent beta-barrel protein. In some embodiments, the treated sample has a concentration of fluorescent protein above about 1 fM. In some embodiments, the treated sample has a concentration of fluorescent protein above about 1 nM.

In some embodiments, the treated sample has a concentration of fluorescent protein above about 10 nM. In some embodiments, the amyloid fibril related species include Aβ, IAPP, amylin, PAPf39, SEMI, α-synuclein, tau, insulin, Huntingtin, PrPSc, Medin, Apolipoprotein AI, Atrial natriuretic factor, β-2 microglobulin, transthyretin, gelsolin, lysozyme, keratoepithelin, calcitonin, prolactin, serum amyloid A, immunoglobulin light chain AL, or combinations and/or variants thereof. In some embodiments, the sample includes blood, blood plasma, urine, seminal fluid, seminal plasma, cerebrospinal fluid, lymphatic fluid, intraocular fluid, synovial fluid, serous fluid, endolymph, perilymph, peritoneal fluid, pleural fluid, pancreatic tissue, brain tissue, liver tissue, heart tissue, thyroid tissue, corneal tissue, a biopharmaceutical, a therapeutic drug, or combinations thereof.

Some embodiments of the disclosed subject matter are directed to a method of inhibiting amyloid fibril formation including providing a reagent including a fluorescent protein to an environment including amyloid monomers. In some embodiments, the method includes binding the fluorescent protein to amyloid oligomers during a lag phase or an elongation phase of amyloid fibril formation.

In some embodiments, the environment includes blood, blood plasma, urine, seminal fluid, seminal plasma, cerebrospinal fluid, lymphatic fluid, intraocular fluid, synovial fluid, serous fluid, endolymph, perilymph, peritoneal fluid, pleural fluid, or combinations thereof. In some embodiments, the reagent is provided during the lag phase. In some embodiments, the treated sample has a concentration of fluorescent protein above about 1.5 μM. In some embodiments, the treated sample has a concentration of fluorescent protein above about 10 μM.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1A:
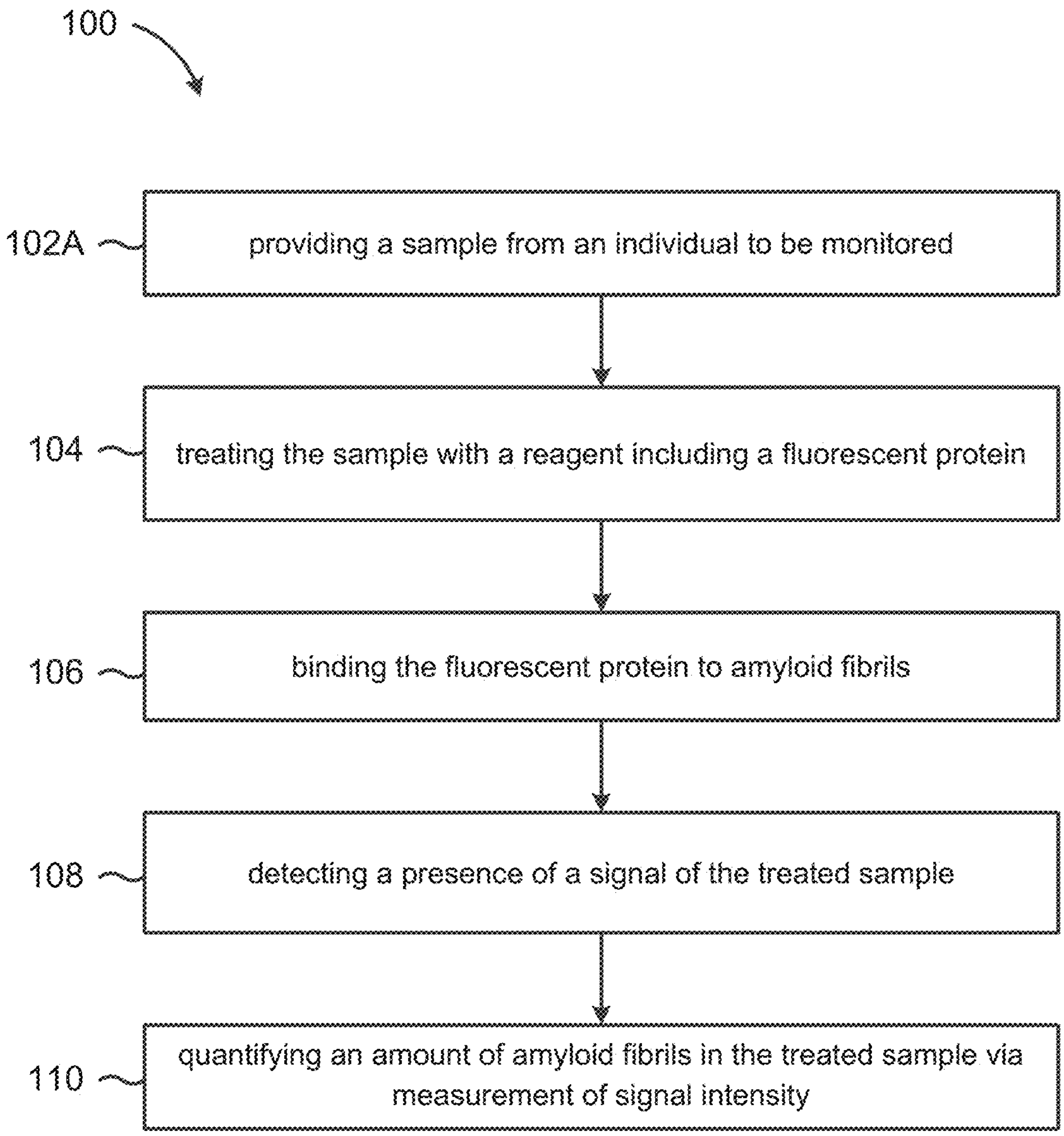
FIG. 1A is a chart of a method for monitoring a sample for the presence of amyloid fibril related species according to some embodiments of the disclosed subject matter.
Figure 1B:
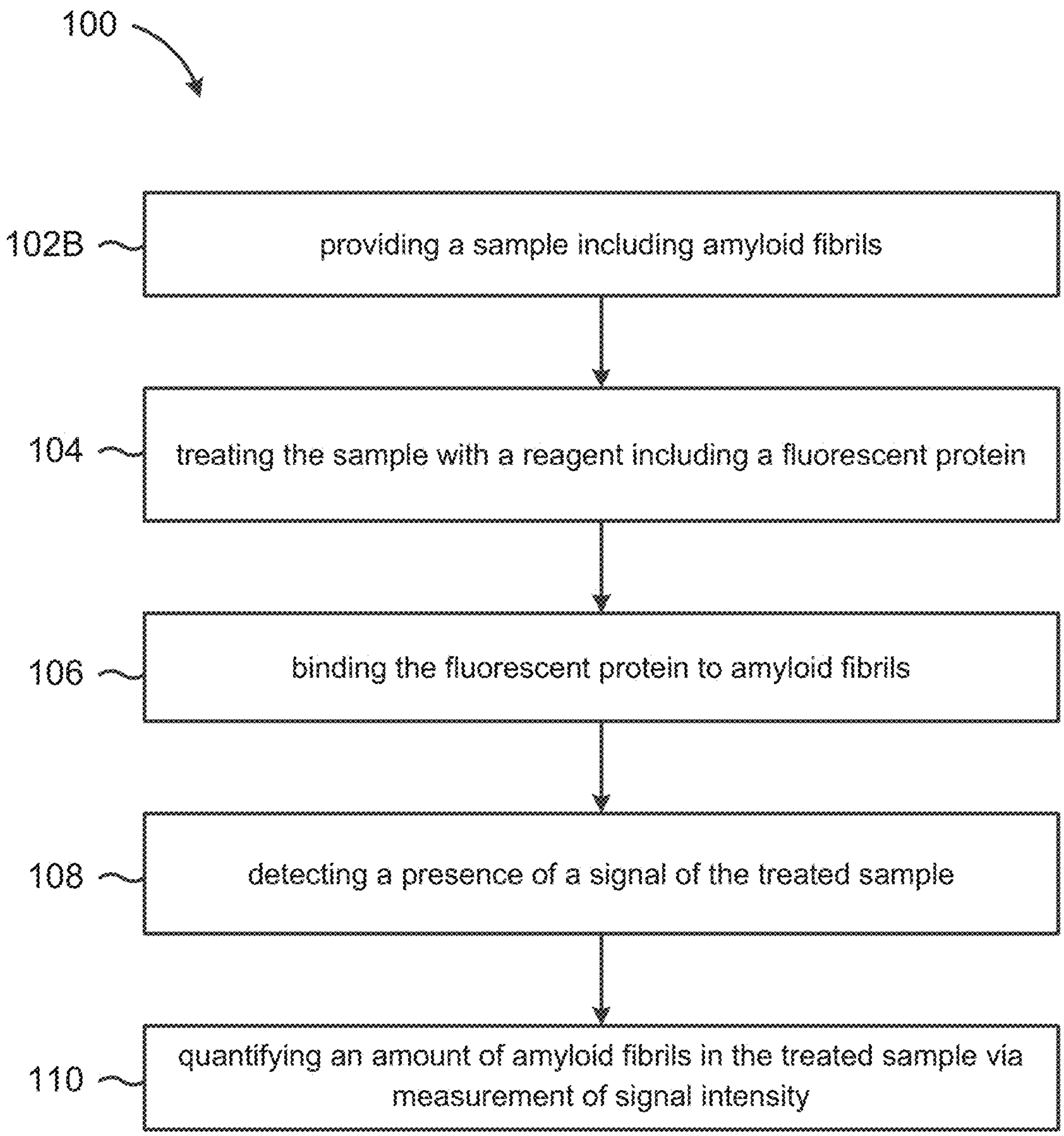
FIG. 1B is a chart of a method for detecting amyloid fibril related species in a sample according to some embodiments of the disclosed subject matter.

Referring now to FIGS. 1A-1B, aspects of the disclosed subject matter include a method 100 of detecting amyloid fibril related species, e.g., amyloid protofibrils, mature amyloid fibrils, amyloid oligomers, or combinations thereof, in a sample. Referring specifically to FIG. 1A, at 102A, a sample is provided from an individual, e.g, a patient, to be monitored for the presence of amyloid fibril related species. Referring specifically to FIG. 1B, at 102B, a sample is provided that includes or is suspected to include amyloid fibril related species. In some embodiments, the sample is a bodily fluid or tissue provided by the individual. In some embodiments, the sample includes blood, blood plasma, urine, seminal fluid, seminal plasma, cerebrospinal fluid, lymphatic fluid, intraocular fluid, synovial fluid, serous fluid, endolymph, perilymph, peritoneal fluid, pleural fluid, pancreatic tissue, brain tissue, liver tissue, heart tissue, thyroid tissue, corneal tissue, a biopharmaceutical, a therapeutic drug, or combinations thereof. In some embodiments, the amyloid fibril related species to be detected include Aβ, IAPP, amylin, PAPf39, SEMI, α-synuclein, tau, insulin, Huntingtin, PrPSc, Medin, Apolipoprotein AI, Atrial natriuretic factor, β-2 microglobulin, transthyretin, gelsolin, lysozyme, keratoepithelin, calcitonin, prolactin, serum amyloid A, immunoglobulin light chain AL, or combinations and/or variants thereof.

Still referring to FIGS. 1A and 1B, at 104, the sample is treated with a reagent including a fluorescent protein. In some embodiments, the fluorescent protein is a cnidarian fluorescent beta-barrel protein. In some embodiments, the fluorescent protein is green fluorescent protein ("GFP"), e.g., as isolated from *Aequorea victoria*; a variant green fluorescent protein, e.g., superfolder GFP, supercharged GFPs, yellow fluorescent protein, etc.; red fluorescent protein, e.g., as isolated from Discosoma sp.; a variant red fluorescent protein, e.g., mCherry; Dendra, e.g., as isolated from octocoral *Dendronephthya* sp.; variant Dendra, e.g., Dendra2; Dronpa, e.g., as isolated from coral Pectiniidae; variant Dronpa, e.g., Dronpa-2; mEosFP; variant mEosFP, e.g., mEos2; or combinations thereof. In some embodiments, treatment step 104 is performed in vitro. In some embodiments, treatment step 104 is performed in vivo.

Figure 2:
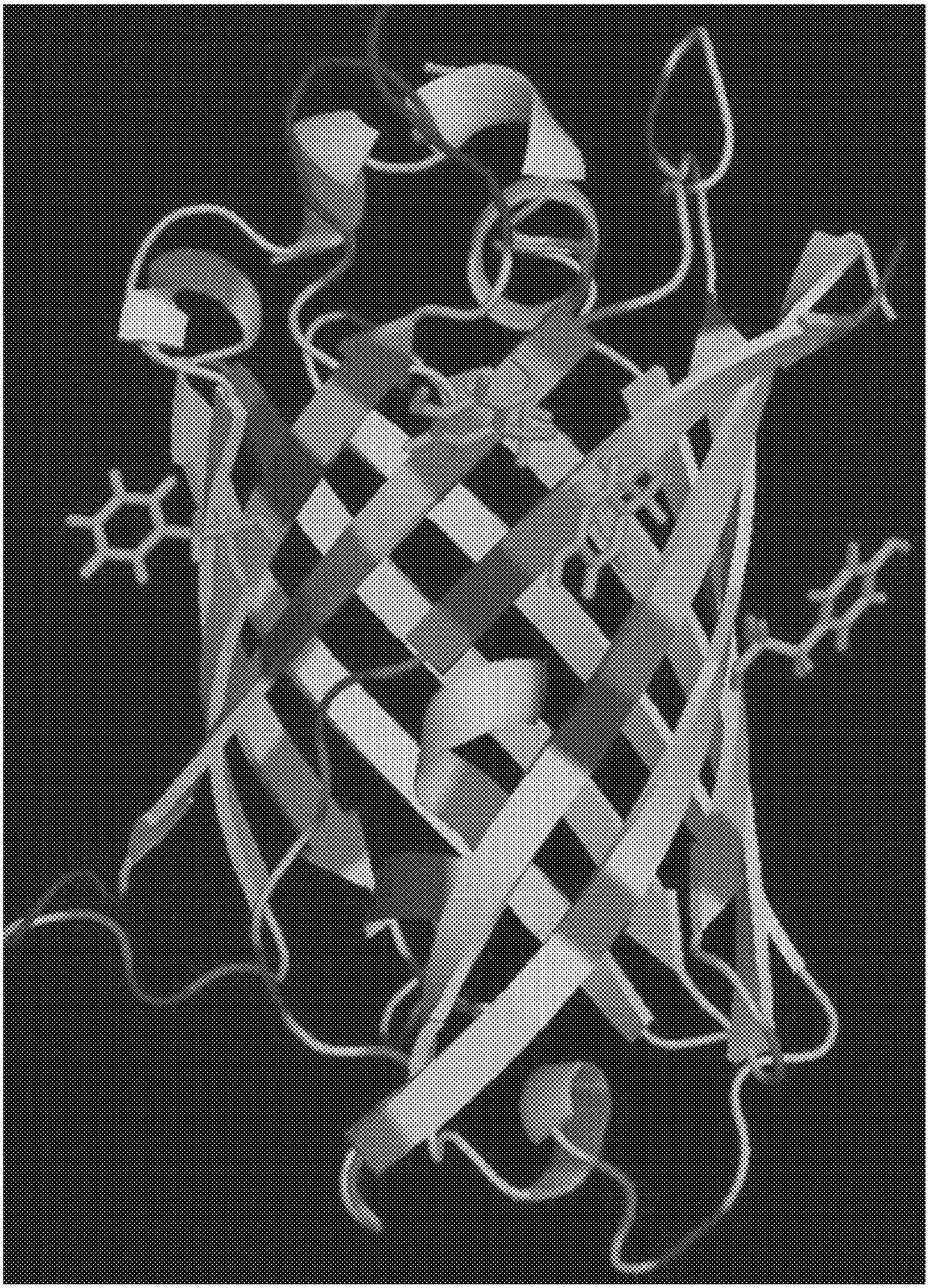
FIG. 2 is a schematic drawing of the structure of green fluorescent protein.

At 106, fluorescent protein from the reagent is bound to the amyloid fibril related species. Without wishing to be bound by any theory of how the fluorescent protein from the reagent is bound to the amyloid fibril related species, and as shown in FIG. 2, aromatic groups disposed on the surface of the β-barrel portion of the fluorescent protein, such as those provided by surface tyrosine and phenylalanine moieties, increase affinity of the fluorescent protein for the amyloid fibril related species. In some embodiments, binding step 106 is performed in vitro. In some embodiments, binding step 106 is performed in vivo. Referring back to FIGS. 1A-1B, at 108, a signal from the treated sample indicating fluorescent protein is bound to the treated sample is detected, indicating the presence of amyloid fibril related species in the sample. In some embodiments, detection 108 includes confocal microscopy, fluorescent microscopy, fluorescent spectroscopy, absorption spectroscopy, ELISA, mass spectroscopy, radioactive detection, etc., or combinations thereof. In some embodiments, detection 108 of the signal from the treated sample is performed in vitro. In some embodiments, detection 108 of the signal from the treated sample is performed in vivo. At 110, the amount of amyloid fibril related species in the sample is quantified via measurement of fluorescence intensity. The signal detection and intensity quantification is measured by any method known to one of skill in the art, including, but not limited to, confocal microscopy, fluorescent microscopy, fluorescent spectroscopy, absorption spectroscopy, ELISA, mass spectroscopy, radioactive detection, etc., or combinations thereof. In some embodiments, the treated sample has a concentration of fluorescent protein above about 1 fM. In some embodiments, the treated sample has a concentration of fluorescent protein above about 1 nM. In some embodiments, e.g., when detecting and/or quantifying native fluorescence, the treated sample has a concentration of fluorescent protein above about 10 nM.

Figure 3:
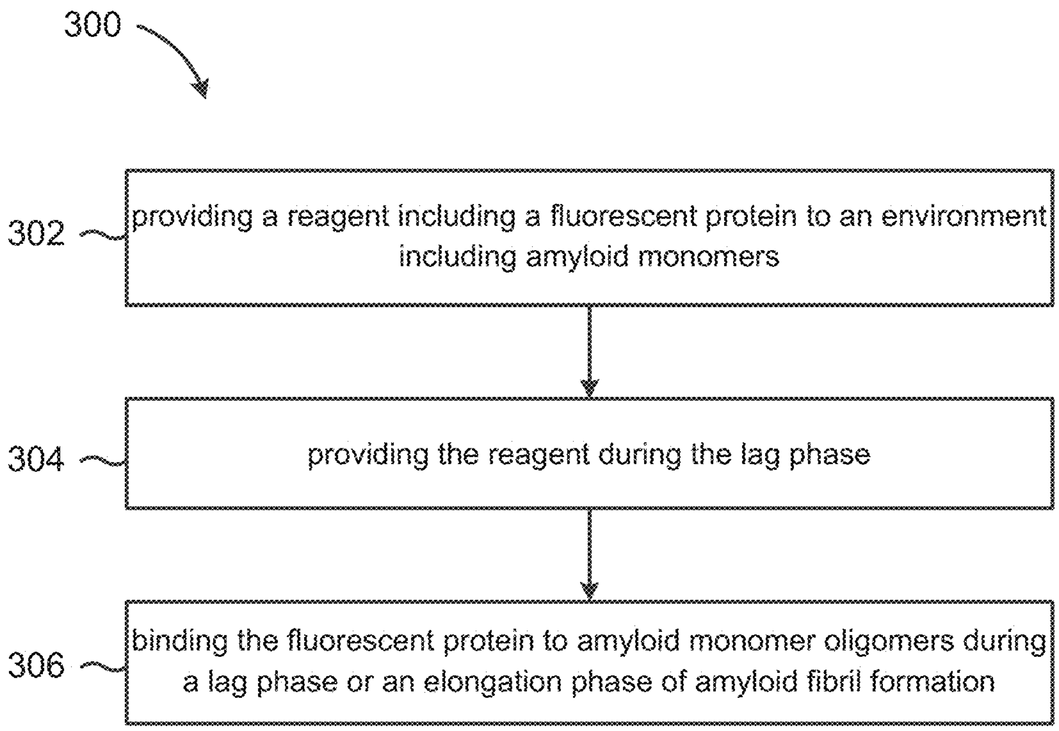
FIG. 3 is a chart of a method for inhibiting amyloid fibril formation according to some embodiments of the disclosed subject matter.

Referring now to FIG. 3, aspects of the disclosed subject matter include a method 300 of inhibiting amyloid fibril formation. At 302, a reagent including a fluorescent protein is provided to an environment including amyloid monomers. In some embodiments, the environment includes blood, blood plasma, urine, seminal fluid, seminal plasma, cerebrospinal fluid, lymphatic fluid, intraocular fluid, synovial fluid, serous fluid, endolymph, perilymph, peritoneal fluid, pleural fluid, or combinations thereof. In some embodiments, at 304, the reagent is provided during the lag phase of amyloid fibril formation. At 306, fluorescent protein is bound to amyloid oligomers. In some embodiments, the fluorescent protein is green fluorescent protein ("GFP"), e.g., as isolated from *Aequorea victoria*; a variant green fluorescent protein, e.g., superfolder GFP, supercharged GFPs, yellow fluorescent proteins, etc.; red fluorescent protein, e.g., as isolated from Discosoma sp.; a variant red fluorescent protein, e.g., mCherry; Dendra, e.g., as isolated from octocoral *Dendronephthya* sp.; variant Dendra, e.g., Dendra2; Dronpa, e.g., as isolated from a coral Pectiniidae; variant Dronpa, e.g., Dronpa-2; mEosFP; variant mEosFP, e.g., mEos2; or combinations thereof. In some embodiments, the fluorescent protein is bound during the lag phase and/or the elongation phase of amyloid fibril formation. In some embodiments, the fluorescent protein is added to the environment to a concentration above about 1.5 μM. In some embodiments, the fluorescent protein is added to the environment to a concentration above about 10 μM. In some embodiments, method 300 is performed at least partially in vitro. In some embodiments, method 300 is performed in vivo.

Figure 4A:
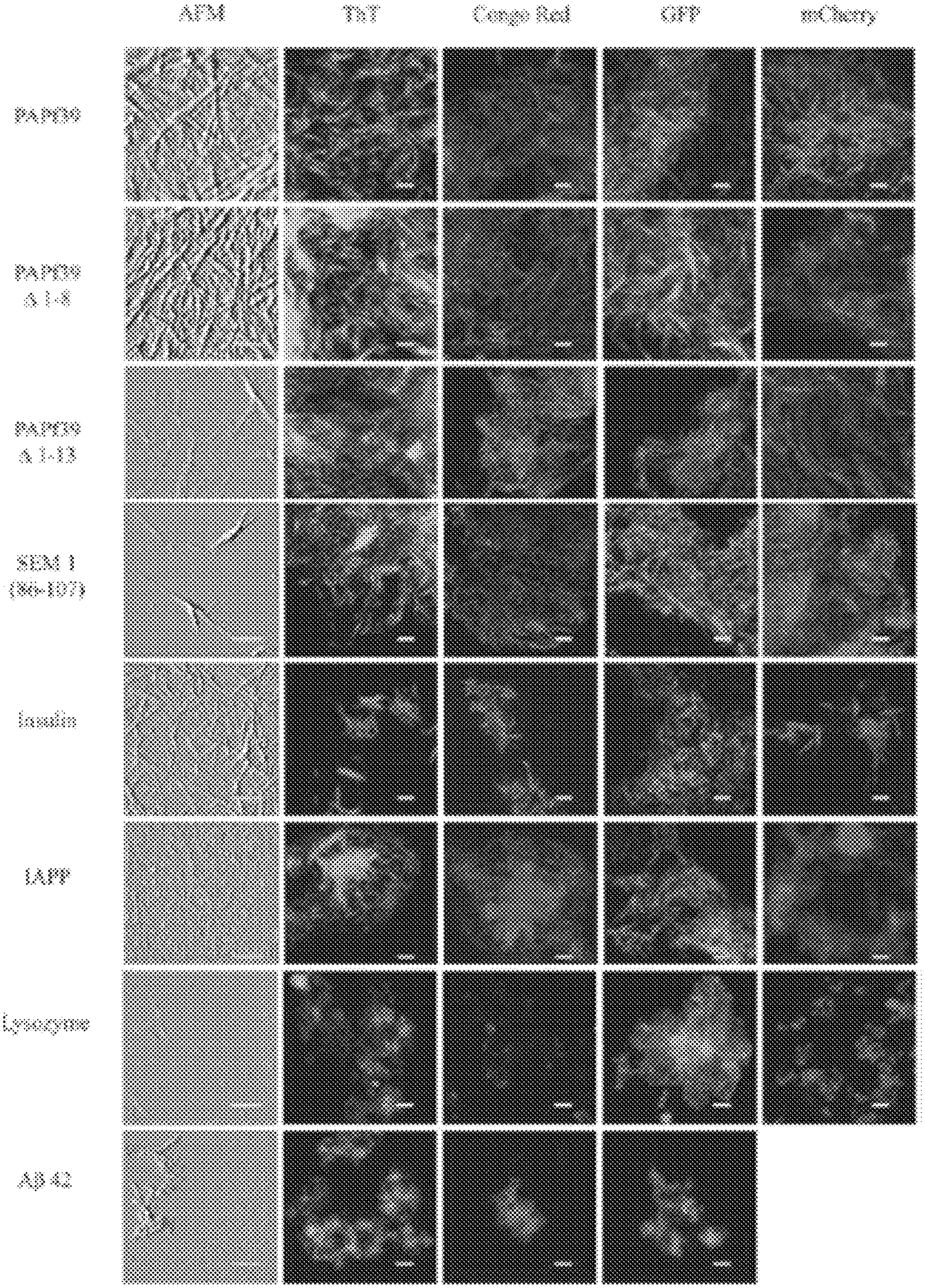
FIGS. 4A and 4B portray the binding specificity of fluorescent protein for amyloid fibrils.
Figure 4B:
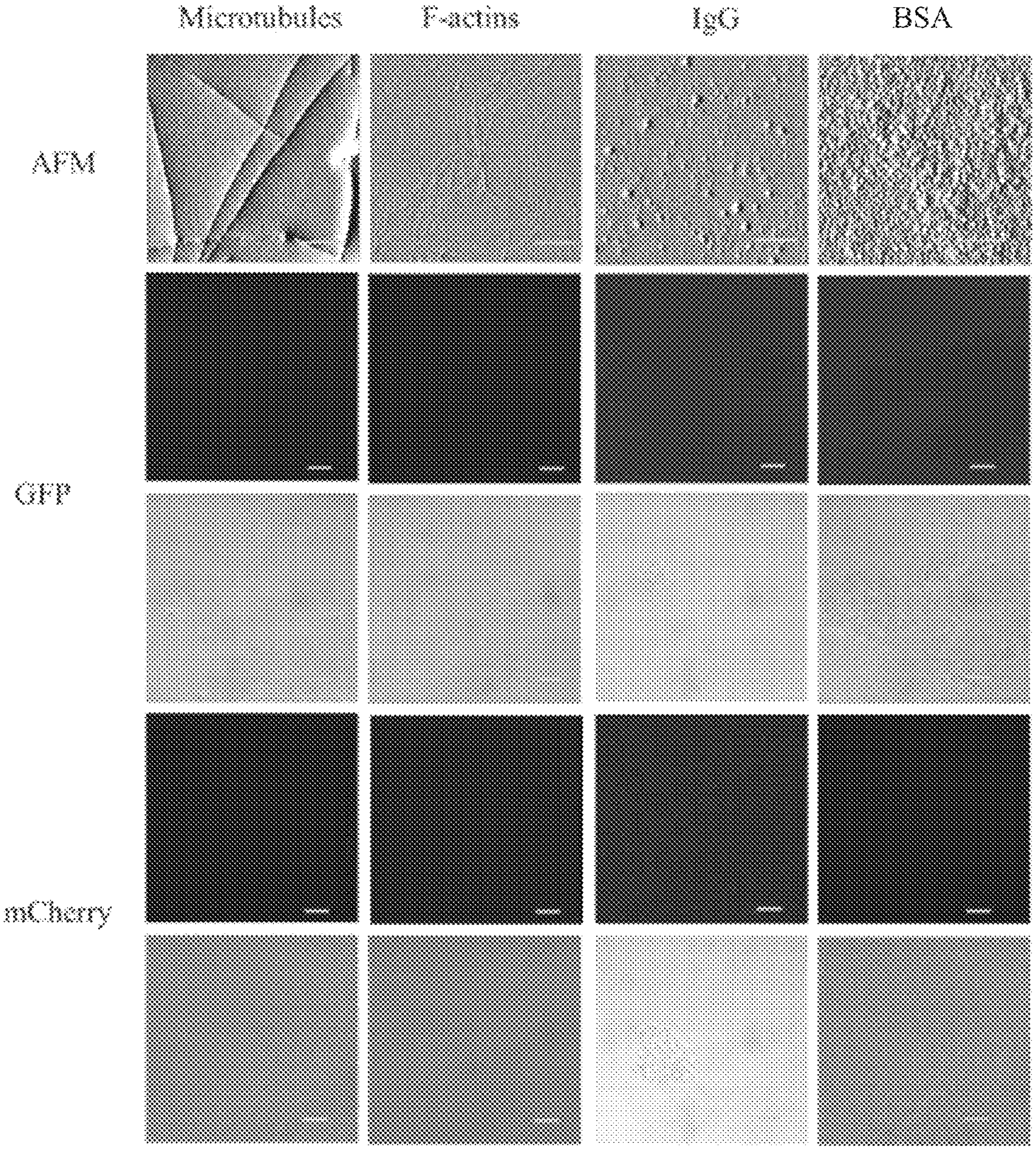

Methods consistent with the present disclosure advantageously detect the presence of amyloid fibril related species in vitro, in situ, ex vivo and in vivo via the binding and detection of fluorescent proteins to them. The presence of amyloid fibril related species has been associated with the presence and/or progression of amyloid diseases. As shown in FIGS. 4A and 4B, fluorescent proteins exhibit a specificity for amyloid fibril related species (FIG. 4A) which mitigate potential false positives from the presence of other fibrous structures (FIG. 4B), such as actins and/or amorphous aggregates, such as denatured IgG or BSA. Thus, if the presence of amyloid disease in an individual is unknown or only suspected, screening for fluorescent protein binding to a fluid or tissue sample from an individual is a useful diagnostic for amyloid disease. Further, for individuals previously diagnosed with an amyloid disease, quantifying the binding of fluorescent protein to fluid and/or tissue samples with respect to time is a useful indicator of the progression or regression of the disease. The methods of the present disclosure can be helpful in the detection and monitoring of diseases including, but not limited to, Alzheimer's disease, Parkinson's disease, Huntington's disease, Creutzfeldt-Jakob disease, aortic medial amyloid, atherosclerosis, cerebral amyloid angiopathy, transmissible spongiform encephalopathy, isolated atrial amyloidosis, diabetes mellitus type 2, dialysis related amyloidosis, familial amyloid polyneuropathy, Finnish amyloidosis, hereditary non-neuropathic systemic amyloidosis, lattice corneal dystrophy, medullary carcinoma of the thyroid, cardiac arrhythmias, prolactinomas, rheumatoid arthritis, systemic AL amyloidosis, sporadic inclusion body myositis, etc. The binding of fluorescent protein to amyloid fibril related species can also have additional advantageous uses, such as targeted delivery of fusion protein including the fluorescent protein and one or more drugs, antibodies, proteases, etc. for detection, quantification, treatment and/or modification of the amyloid fibril related species. The binding of fluorescent protein to amyloid fibril related species can also advantageously be used to remove amyloid fibril related species from a sample, e.g., fibrils that accumulate during production, formulation, transportation, and storage of biopharmaceuticals, therapeutic drugs, and other liquid media, or alpha-2-macroglobulin fibrils during renal dialysis.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of detecting amyloid fibril related species, the method comprising:
providing a sample including amyloid fibril related species;
treating said sample with a fluorescent protein selected from the group consisting of: green fluorescent protein, a variant green fluorescent protein, red fluorescent protein, Dendra, variant Dendra, Dronpa, variant Dronpa, mEosFP, variant mEosFP, or combinations thereof;
binding said fluorescent protein to the amyloid fibril related species; and
detecting a signal from fluorescent protein bound to said treated sample.

2. The method according to claim 1, further comprising quantifying an amount of amyloid fibril related species in said treated sample via measurement of signal intensity.

3. The method according to claim 1, wherein detecting said signal from fluorescent protein bound to said treated sample further comprises confocal microscopy, fluorescent microscopy, fluorescent spectroscopy, absorption spectroscopy, ELISA, mass spectroscopy, radioactive detection, or combinations thereof.

4. The method according to claim 1, wherein said treated sample has a concentration of fluorescent protein above about 1 nM.

5. The method according to claim 1, wherein said amyloid fibril related species include Aβ, IAPP, amylin, PAPf39, SEMI, α-synuclein, tau, insulin, Huntingtin, PrPSc, Medin, Apolipoprotein AI, Atrial natriuretic factor, β-2 microglobulin, transthyretin, gelsolin, lysozyme, keratoepithelin, calcitonin, prolactin, serum amyloid A, immunoglobulin light chain AL, or combinations or variants thereof.

6. The method according to claim 1, wherein said sample includes blood, blood plasma, urine, seminal fluid, seminal plasma, cerebrospinal fluid, lymphatic fluid, intraocular fluid, synovial fluid, serous fluid, endolymph, perilymph, peritoneal fluid, pleural fluid, pancreatic tissue, brain tissue, liver tissue, heart tissue, thyroid tissue, corneal tissue, a biopharmaceutical, a therapeutic drug, or combinations thereof.

7. The method according to claim 1, wherein the fluorescent protein is wild-type green fluorescent protein.

8. A method of inhibiting amyloid fibril formation, the method comprising:
providing a fluorescent protein to an environment including amyloid monomers, the fluorescent protein selected from the group consisting of: green fluorescent protein, a variant green fluorescent protein, red fluorescent protein, Dendra, variant Dendra, Dronpa, variant Dronpa, mEosFP, variant mEosFP, or combinations thereof; and
binding said fluorescent protein to amyloid monomer oligomers during a lag phase or an elongation phase of amyloid fibril formation.

9. The method according to claim 8, wherein providing said fluorescent protein to an environment including amyloid monomers further comprises:
providing said fluorescent protein during said lag phase.

10. The method according to claim 8, wherein said environment includes blood, blood plasma, urine, seminal fluid, seminal plasma, cerebrospinal fluid, lymphatic fluid, intraocular fluid, synovial fluid, serous fluid, endolymph, perilymph, peritoneal fluid, pleural fluid, or combinations thereof.

11. The method according to claim 8, wherein the fluorescent protein is wild-type green fluorescent protein.

12. The method according to claim 8, wherein said environment has a concentration of fluorescent protein above about 1.5 μM.

13. The method according to claim 12, wherein said environment has a concentration of fluorescent protein above about 10 μM.

14. A method of monitoring for the presence or progression of amyloid diseases, the method comprising:
providing a sample from an individual to be monitored;
treating said sample with a fluorescent protein selected from the group consisting of: green fluorescent protein, a variant green fluorescent protein, red fluorescent protein, Dendra, variant Dendra, Dronpa, variant Dronpa, mEosFP, variant mEosFP, or combinations thereof; and
detecting a signal from fluorescent protein bound to said treated.

15. The method according to claim 14, further comprising quantifying an amount of amyloid fibril related species in said treated sample via measurement of signal intensity.

16. The method according to claim 14, wherein detecting said signal from fluorescent protein bound to said treated sample further comprises confocal microscopy, fluorescent microscopy, fluorescent spectroscopy, absorption spectroscopy, ELISA, mass spectroscopy, radioactive detection, or combinations thereof.

17. The method according to claim 14, wherein said amyloid fibril related species include Aβ, IAPP, amylin, PAPf39, SEMI, α-synuclein, tau, insulin, Huntingtin, PrPSc, Medin, Apolipoprotein AI, Atrial natriuretic factor, β-2 microglobulin, transthyretin, gelsolin, lysozyme, keratoepithelin, calcitonin, prolactin, serum amyloid A, immunoglobulin light chain AL, or combinations or variants thereof.

18. The method according to claim 14, wherein said sample includes blood, blood plasma, urine, seminal fluid, seminal plasma, cerebrospinal fluid, lymphatic fluid, intraocular fluid, synovial fluid, serous fluid, endolymph, perilymph, peritoneal fluid, pleural fluid, pancreatic tissue, brain tissue, liver tissue, heart tissue, thyroid tissue, corneal tissue, a biopharmaceutical, a therapeutic drug, or combinations thereof.

19. The method according to claim 14, wherein said treated sample has a concentration of fluorescent protein above about 1 nM.

20. The method according to claim 14, wherein the fluorescent protein is wild-type green fluorescent protein.

* * * * *